United States Patent [19]

Geschickter

[11] Patent Number: 4,468,393

[45] Date of Patent: Aug. 28, 1984

[54] TREATMENT OF ARTHRITIS

[75] Inventor: Charles F. Geschickter, Lorton, Va.

[73] Assignee: Unimed, Inc., Somerville, N.J.

[21] Appl. No.: 446,949

[22] Filed: Dec. 6, 1982

[51] Int. Cl.³ ............................................ A61K 31/555
[52] U.S. Cl. .................................................... 424/245
[58] Field of Search ............................ 424/248.4, 245; 260/429 R

[56] References Cited

U.S. PATENT DOCUMENTS 3,825,546 7/1974 Rice .................................. 260/293.66

Primary Examiner—Stanley J. Friedman
Attorney, Agent, or Firm—Steinberg & Raskin

[57] ABSTRACT

Arthritis is treated by administration of azaspirane compounds, either germanium or silicon azaspirane compounds, preferably spirogermanium, most preferably dimethyl, diethyl, dipropyl or dibutyl. The diethyl or dibutyl are the most preferred.

4 Claims, No Drawings

TREATMENT OF ARTHRITIS

BACKGROUND OF THE INVENTION

Aside from the treatment of the pain associated with arthritis, with pain relievers such as aspirin and the like, the most beneficial results obtained in the management of arthritis is with the use of cortisone. Cortisone has, however, many limitations in its use, and there is considerable research for other drugs to be used in the management of arthritis.

U.S. Pat. No. 3,825,546 discloses a series of azaspiranes containing silicon or germanium in a ring, in connection with the treatment of cancer.

SUMMARY OF THE INVENTION

Generally speaking, in accordance with the present invention, it has been discovered that certain specific compounds of U.S. Pat. No. 3,825,546, namely those which contain germanium in the ring, that is the spirogermaniums, particularly the dimethyl, diethyl, dipropyl and dibutyl spirogermaniums, including their acid addition salts and bis-quaternary salts, can be used in the treatment of arthritis.

It is accordingly a primary object of the present invention to provide for methods of treating arthritis.

It is a further object of the present invention to provide for the treatment of arthritis by the administration of an arthritis treatment effective amount of a spirogermanium.

Other objects and advantages of the present invention will be apparent from a further reading of the specification and of the appended claims.

The compounds of U.S. Pat. No. 3,825,546 which can be used for the purposes of the present invention are those compounds of the following structural formula:

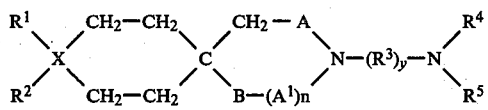

wherein
$R^1$ and $R^2$ are the same or different alkyl groups of 1-4 carbon atoms
x = germanium
A and $A^1$ are the same and either

n = 0 or 1
B = $CH_2$ when n is one and B is the same as A when n is zero
$R^3$ = alkylene or alkenylene
y = 2-6 when $R^3$ is alkylene and 3-4 when $R^3$ is alkenylene
$R^4$ and $R^5$ are the same or different lower alkyls having 1-4 carbon atoms, lower alkenyls having 3-4 carbon atoms, or cyclicized together form a heterocyclic group selected from morpholino, pyrrolidino, piperidino and lower alkyl (1-4 carbon atoms) piperazino in which said lower alkyl is attached to a terminal nitrogen atom, as well as acid addition salts and bis-quarternary salts thereof.

The acid addition salts are of course the physiologically compatible acid addition salts, most preferably the dihydrochloride.

The bis-quaternary salts are of course the physiologically compatible bis-quaternary salts including the methiodide and the dimethiodide.

The dimethyl spirogermanium, diethyl spirogermanium, dipropyl spirogermanium and dibutyl spirogermanium which are effective in the treatment of arthritis are:

N-(3-dimethylaminopropyl)-2-aza-8,8-dimethyl-8-germaspiro[4:5] decane;

N-(3-dimethylaminopropyl)-2-aza-8,8-diethyl-8-germaspiro[4:5] decane;

N-(3-dimethylaminopropyl)-2-aza-8,8-dipropyl-8-germaspiro[4:5] decane; and

N-(3-dimethylaminopropyl)-2-aza-8,8-dibutyl-8-germaspiro[4:5] decane.

As indicated previously, the above compounds may be utilized in the form of their acid addition salts or bis-quaternary salts. Most preferred are the dihydrochloride salts.

The above compounds may be distributed in any suitable pharmaceutical carrier for administration by injection or for oral administration. Aqueous solutions can be prepared of the non-toxic salts which are soluble in water for administration by injection, for example intravenous administration or intraperitoneal injection, or for oral administration. It is preferred, however, for oral administration to utilize compositions in tablet form, for example tablets with lactose or the like as a carrier.

Although the spirogermaniums can be tolerated in rather high doses without any adverse effects, it having been found safe when given intravenously in doses of 50-80 mg/m² of body surface, and even doses of 120 mg/m² of body surface, much smaller doses can be administered for the purposes of the present invention.

The recommended dose of spirogermanium therapy for the treatment of arthritis with severe rheumatoid symptoms is 1.5 cc intramuscularly of an aqueous solution of 30 mg/ml (45 mg/dose). Such treatment is given twice weekly for the first six weeks and once weekly thereafter until remission is obtained. This usually requires 3-6 months of treatment.

Oral treatment can be effected by means of capsules containing 200 mg per capsule, beginning with two capsules daily for two weeks and one capsule daily thereafter for six weeks.

For bouts of severe pain and disability, an intravenous drip of 10 cc spirogermanium (10 mg/ml) diluted in 100 cc distilled water may be administered over a period of one to two hours.

Initial testing of the compositions of the present invention for the treatment of arthritis was effected by administration thereof to cancer patients with a chronic history of arthritis unrelieved by other methods of treatment. The major indication for the therapy for this initial testing was the presence of malignant disease in these individuals. In tests which will be described below, two of the patients had carcinoma of the breast, either with recurrence or metastasis and one had carcinoma of the lung that was inoperable. Beneficial results were achieved, and the clinical history of patients are summarized below.

DESCRIPTION OF THE PREFERRED EMBODIMENTS

The following examples are given to further illustrate the present invention. The scope of the invention is not, however, meant to be limited to the specific details of the examples.

EXAMPLE I

A composition for injection was prepared of diethylspirogermanium dissolved in saline. The solution contained 100 mg spirogermanium per each 10 ml saline.

EXAMPLE II

A composition for injection was prepared of diethylspirogermanium dissolved in water. The solution contained 200 mg spirogermanium per each 10 ml of solution.

EXAMPLE III

All compositions were prepared by forming tablets of diethylspirogermanium and beta lactose with concentrations of 200 mg diethylspirogermanium per tablet. Capsules of the same composition were prepared.

The following is a description of clinical case histories of arthritic patients treated in accordance with the present invention.

A patient (F. G.) was first seen for arthritis at the age of 37. Salicylate therapy was only moderately successful and the patient received injections of ACTHAR Gel for bouts of severe pain during several intervals. The patient developed a cyst of the right breast, which was treated by aspiration and later a small breast nodule appeared in the left breast, which was excised and proved to be cancer. Radical breast surgery was refused by the patient. Post-operation irradiation was administered. Her arthritic symptons varied in intensity from time to time. The patient received alternate injections of silicone and germanium azaspiranes for 2 months followed by injections of germanium azaspirane, namely diethylspirogermanium, (20 mg/ml) injected intramuscularly (in aqueous solution) twice weekly for 5 months.

In the next 60 days, because of the presence of a recurrence of her mammary tumor, injections of germanium azaspirane (25 mg/ml intramuscularly) were given three times weekly for one month followed by injections twice weekly. The patient remained free of all arthritic symptons as well as absence of clinical evidence of her malignant disease for over one year.

A 75 year old white female (I. G.) had mammary cancer treated by simple mastectomy with a recurrent mass appearing in the scar about 2 years later and lymph node involvement in the axilla after an additional 12 months. Metastatic cancer occurred in the skin and in the bone with a pathologic fracure of the right femur several years later.

Arthritic pains with disabling symptons had complicated the long history of her illness and the patient was bedridden when injections of spirogermanium were started 3 times weekly at a dose of 45 mg/dose. Spirogermanium injections were continued with steady improvement of mobility and relief of pain for about 15 months. The patient later died suddenly of myocardial infarction.

A married woman (M. G.) aged 65 had increasing osteoarthritis of the lumbar spine and both knees for a period of 6 years. In the last several years, rheumatoid arthritis affected the hands, knees and elbows. She had been able to pursue her hobbies of knitting and oil painting until the last 3 years. Following a period of cough, pain in the left arm, and night sweats for 3 weeks duration, roentgenograms revealed a carcinoma of the left lung. This was confirmed by thorocotomy.

Spirogermanium therapy was started. Injections were given 3 times weekly in doses of 45 to 60 mg/ml intramuscularly. All arthritic symptoms subsided after the first week of injections. This treatment was continued for 6 months. A total of 2.2 grams of this compound had been administered during this period of approximately 6 months.

While the invention has been described in particular with respect to specific treatments of arthritic conditions, it is apparent that variations and modifications of the invention can be made without parting from the spirit or scope thereof.

What is claimed is:

1. Method of treating arthritis, which comprises administering to a patient suffering from the same an arthritic treatment effective amount of a spirogermanium selected from the group consisting of
N-(3-dimethylaminopropyl)-2-aza-8,8-dimethyl-8-germanspiro[4:5] decane;
N-(3-dimethylaminopropyl)-2-aza-8,8-diethyl-8-germaspiro[4:5] decane;
N-(3-dimethylaminopropyl)-2-aza-8,8-dipropyl-8-germaspiro[4:5] decane; and
N-(3-dimethylaminopropyl)-2-aza-8,8-dibutyl-8-germaspiro[4:5] decane.

2. Method according to claim 1 wherein the administration is by intramuscular injection.

3. Method according to claim 1 wherein the administration is oral.

4. Method according to claim 1 wherein the administration is by intravenous drip.

* * * * *